United States Patent [19]
Mueller

[11] Patent Number: 5,782,823
[45] Date of Patent: Jul. 21, 1998

[54] LASER DEVICE FOR TRANSMYOCARDIAL REVASCULARIZATION PROCEDURES INCLUDING MEANS FOR ENABLING A FORMATION OF A PILOT HOLE IN THE EPICARDIUM

[75] Inventor: Richard L. Mueller, Byron, Calif.

[73] Assignee: Eclipse Surgical Technologies, Inc., Sunnyvale, Calif.

[21] Appl. No.: 628,456

[22] Filed: Apr. 5, 1996

[51] Int. Cl.⁶ .................................................. A61B 17/36
[52] U.S. Cl. ........................... 606/7; 606/11; 606/15
[58] Field of Search ............................ 606/7, 10, 11, 606/13–16; 607/89

[56] References Cited

U.S. PATENT DOCUMENTS

| | | | |
|---|---|---|---|
| 4,658,817 | 4/1987 | Hardy | 606/14 |
| 4,846,171 | 7/1989 | Kauphusman et al. | 606/16 |
| 5,554,152 | 9/1996 | Aita et al. | 606/7 |

FOREIGN PATENT DOCUMENTS

| | | | |
|---|---|---|---|
| 0515867 A2 | 2/1992 | European Pat. Off. | |
| WO 94/14383 A1 | 7/1994 | WIPO | |

*Primary Examiner*—Ruth S. Smith
*Attorney, Agent, or Firm*—Roger W. Erickson; Janet Kaiser Castaneda; Christopher N. Sears

[57] ABSTRACT

An apparatus for performing a laser myocardial revascularization of a human heart comprises a hand-held device with an elongated flexible lasing assembly including an axially movable fiber bundle which can be placed into the chest cavity of a patient. At the distal head end of the device laser energy from the distal end of the fiber bundle is initially reduced to form a relatively small opening in the epicardium of the heart. The fiber bundle is moved through the opening so that lasing with full laser power takes place beneath the epicardium to form a larger channel through the myocardium that extends into the left ventricular cavity. After the channel has been formed, the optical fiber bundle is retracted from the channel and back through the small epicardium opening so as to minimize operative bleeding and allow sealing of the epicardium after the apparatus is removed.

19 Claims, 5 Drawing Sheets

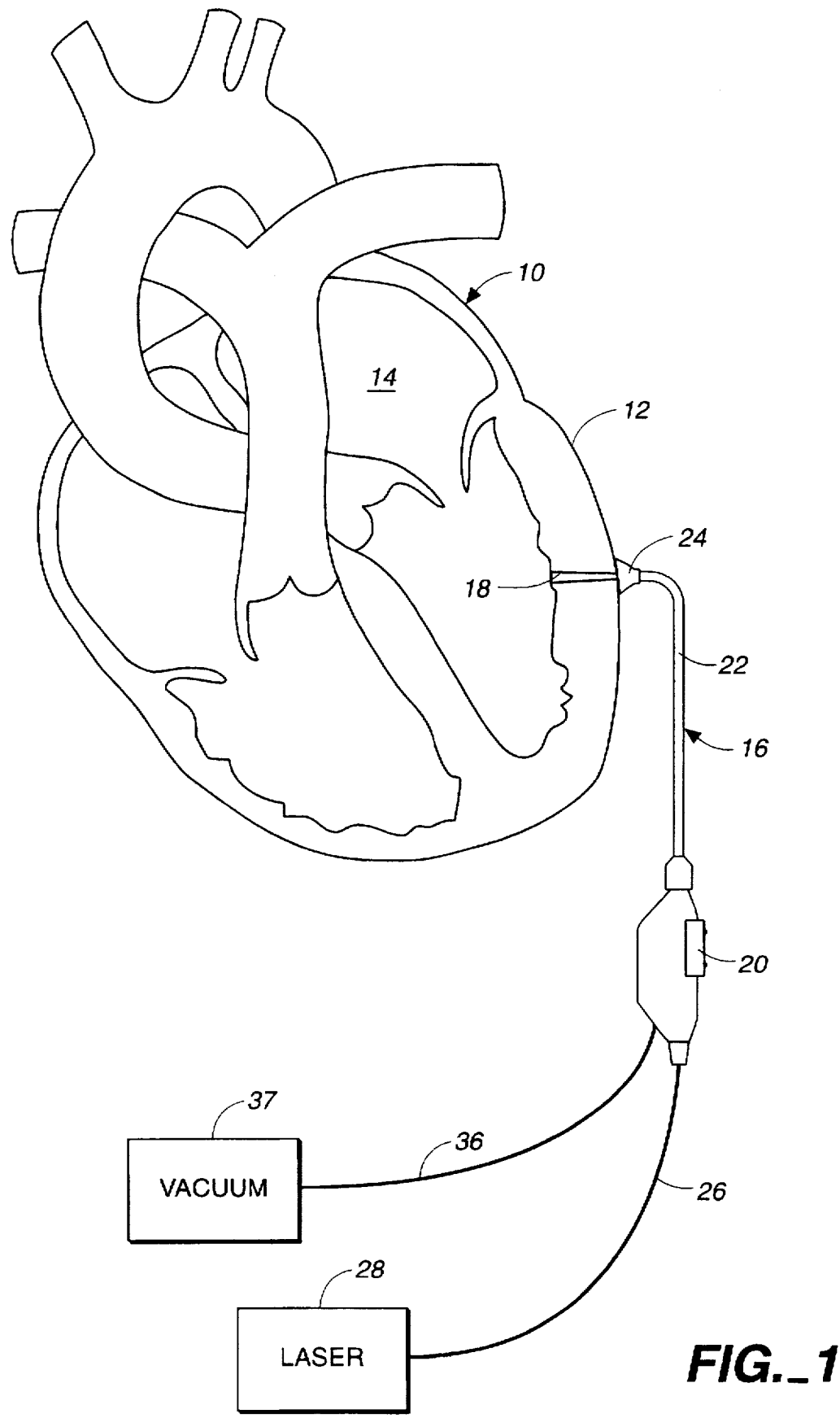
FIG._1

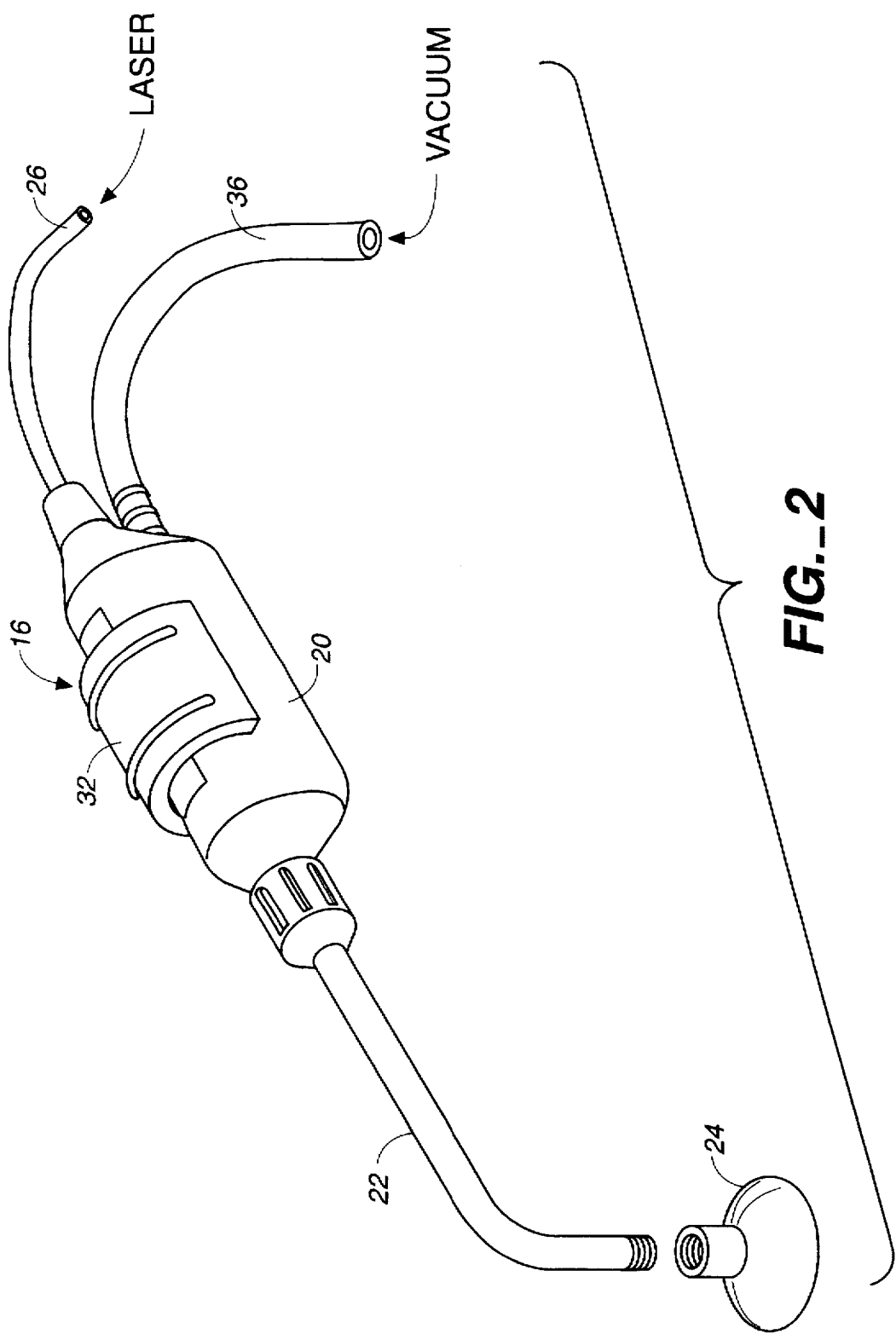
FIG._2

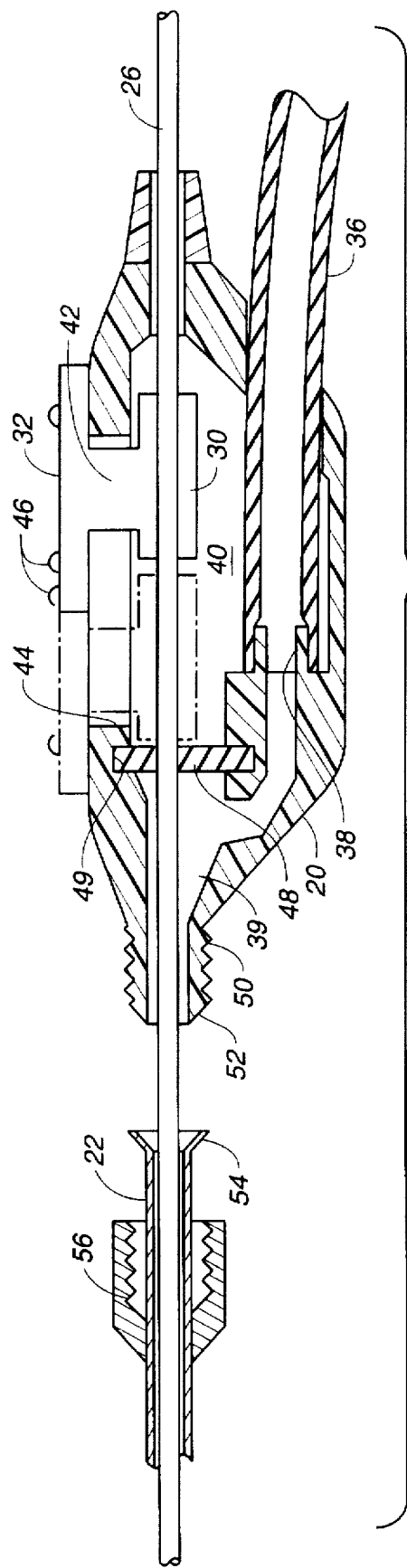
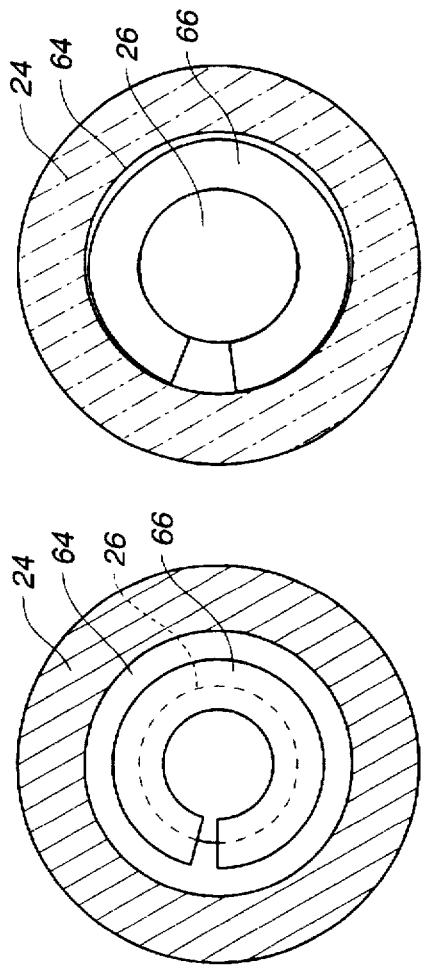
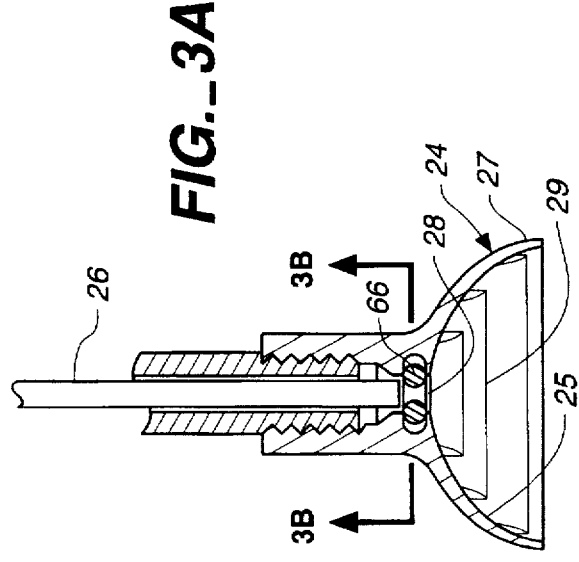
FIG._3
FIG._3C
FIG._3B
FIG._3A

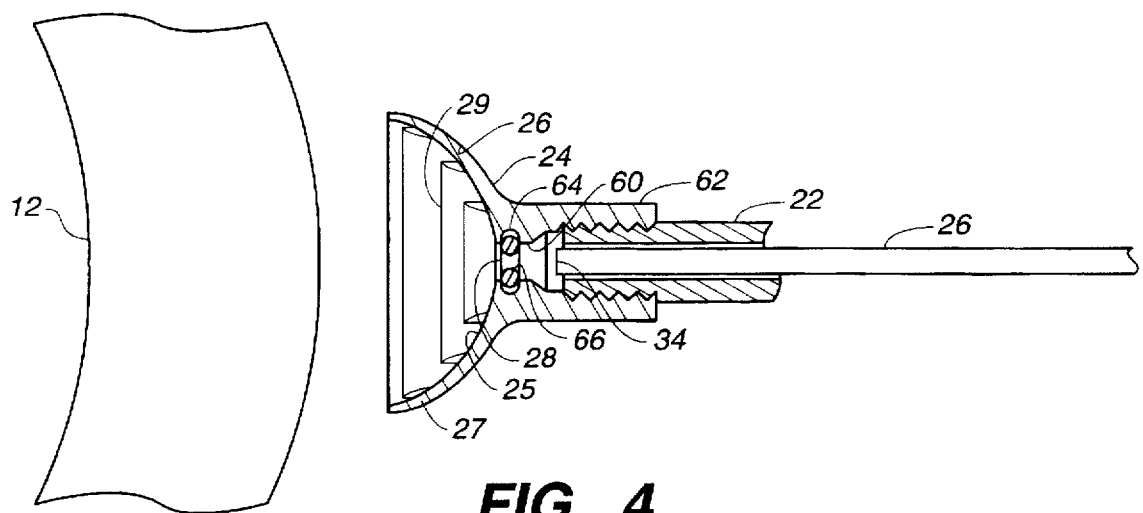
FIG._4
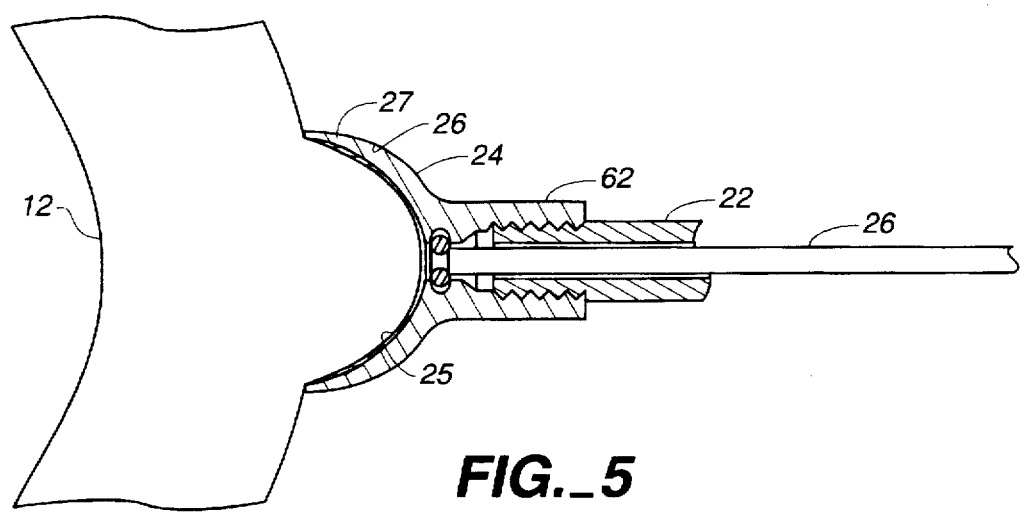
FIG._5
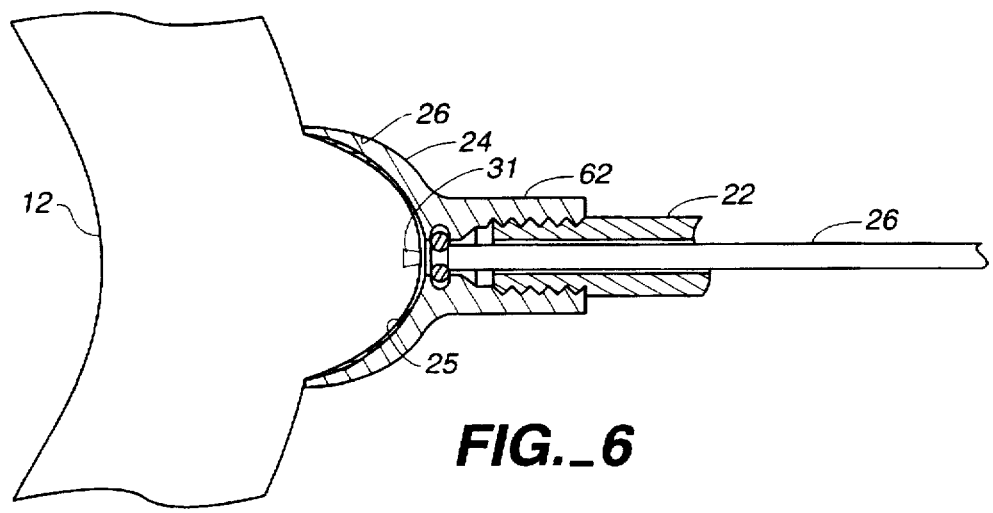
FIG._6

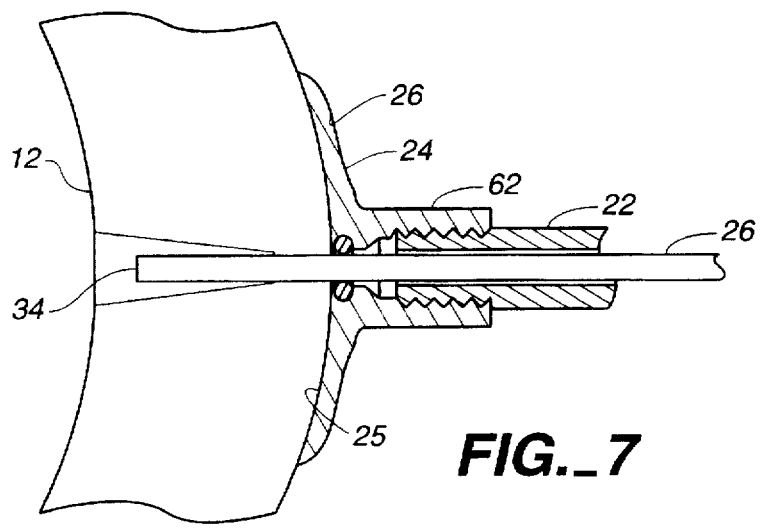
FIG._7
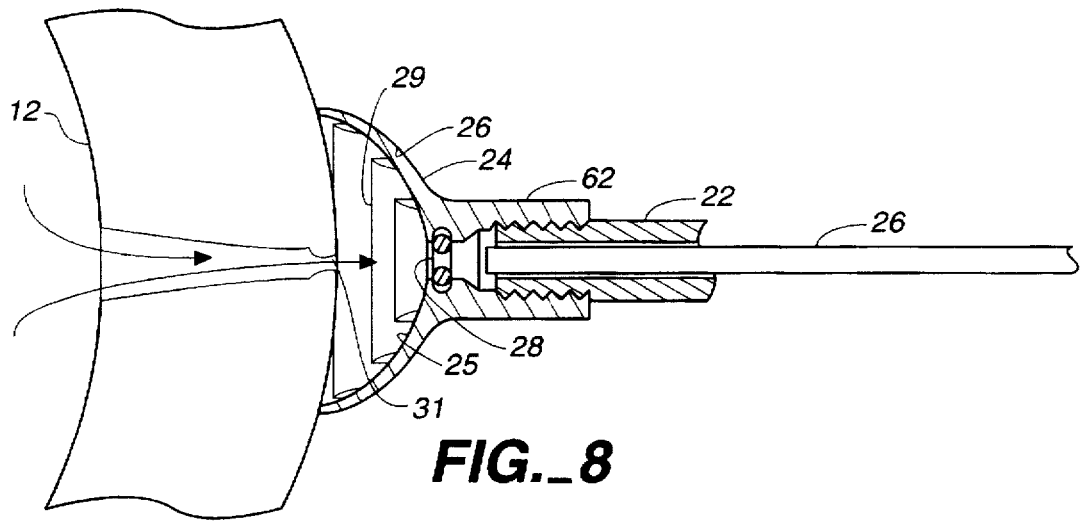
FIG._8
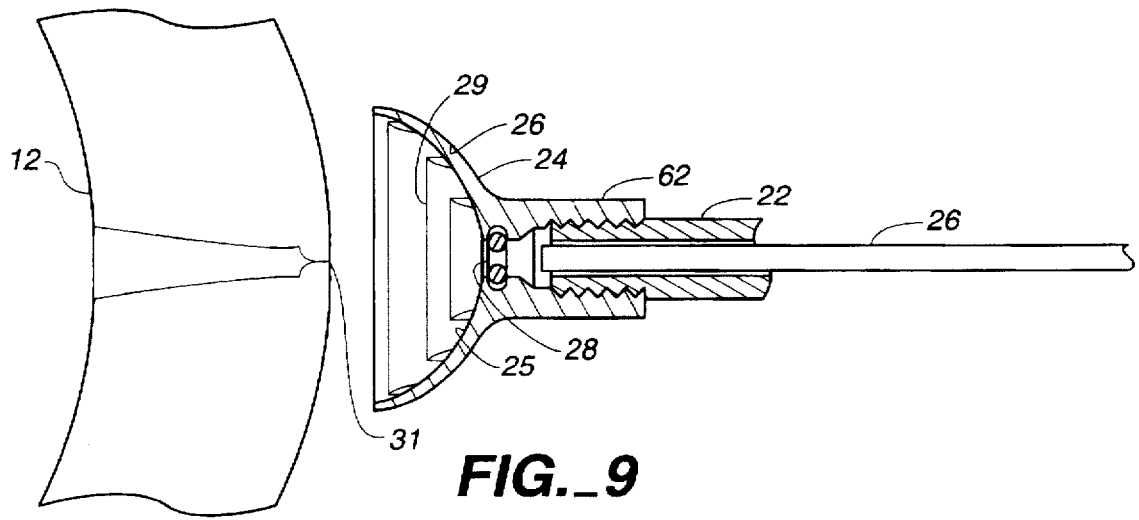
FIG._9

LASER DEVICE FOR TRANSMYOCARDIAL REVASCULARIZATION PROCEDURES INCLUDING MEANS FOR ENABLING A FORMATION OF A PILOT HOLE IN THE EPICARDIUM

FIELD OF THE INVENTION

This invention relates to the field of laser surgery, and more particularly to an improved laser surgery device for use in procedures for increasing the flow of blood to heart muscle.

BACKGROUND OF THE INVENTION

Medical science has developed a wide variety of methods for counteracting the effects of cardiovascular disease including open heart and by-pass surgery. Non-surgical procedures such as percutaneous transluminal coronary angioplasty, laser angioplasty, and atherectomy have also been developed.

One alternative to the aforementioned procedures is known as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. The resultant channel through the myocardium was funnel-like. A problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al U.S. Pat. No. 5,380,316. Aita, commenting on the Hardy needle device, contends that mechanical piercing was undesirable because it entailed some degree of tearing of the pierced tissue, and that tearing often leads to fibrosis as the mechanical tear heals, a factor that severely diminishes the effectiveness of the TMR treatment. Aita, et al also contends that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini TMR procedure with respect to the aforementioned bleeding problem in the outer surface of the epicardium.

In a copending application Ser. No. 08/607,782 which is assigned to the assignee of the present application, an improved apparatus and method for TMR procedures is disclosed. In this application the epicardium membrane of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed the opening that was made mechanically in the epicardium tends to close to prevent excessive bleeding from the channel formed in the myocardium.

Under certain operating conditions, the characteristics of the epicardium membrane may vary so the physician may elect to use an alternate means on the hand-held device for penetrating the epicardium membrane during a TMR procedure which minimizes bleeding after the procedure has been completed. Thus, it is desirable that the physician be able to pierce the epicardium in the most efficient manner and thereby minimize the size of the opening necessary to accommodate the advancing fiber element. The improved TMR device of the present invention solves these problems.

It is therefore a general object of the present invention to provide an improved apparatus for performing laser myocardial revascularization that solves the problems of the aforementioned prior devices and procedures.

A further object of the present invention is to provide a less invasive and safer apparatus for performing laser myocardial revascularization which does not diminish the effectiveness of the TMR treatment and eliminates the problem of excessive bleeding from the patient's epicardium following the channel forming procedure.

It is a further object of the present invention to provide an apparatus for performing laser myocardial revascularization which utilizes a reduced laser pulse to form a preliminary perforation opening in the epicardium membrane to enable the passage of an optical fiber means for forming a widened channel in the myocardium and such a way as to minimize bleeding from and promote sealing of the epicardium opening.

Still another object of the present invention is to provide an improved device for performing a TMR procedure wherein an initial small opening is formed in the epicardium to facilitate formation of a larger cone-shaped channel whose wider end is at the endocardium to promote blood perfusion from the left ventricular cavity and whose narrow end is closed beneath the epicardium to avoid excessive epicardial bleeding after the procedure.

Yet another object of the invention is to provide a device for use in a TMR procedure which uses a concave distal end member that contacts the outer surface of the epicardium, and then applies air suction during the procedure to draw the epicardium into the distal end member and thereafter draw blood into the channel just formed, thereby enhancing the effectiveness of the procedure.

SUMMARY OF THE INVENTION

The present invention comprises a method and apparatus for combined mechanical/laser myocardial revascularization of a human heart that fulfills the aforesaid objectives. A hand-held device which includes an elongated flexible lasing apparatus including an optical fiber bundle that can be is inserted into the chest cavity of a patient. In one form, the device includes a detachable distal head end assembly including a circular, disk having a central bore through which the distal tip of the fiber bundle can pass. A restrictive sensing and positioning means is provided in the bore for momentarily stopping the distal end of the fiber bundle at an optimum distance from the surface of the epicardium. This positioning means provides a temporary peripheral shield which reduces the amount of laser energy from the fiber bundle by decreasing the diameter of the laser beam emitted from its distal end. When at this preliminary position against the sensing means, a laser pulse is initiated to emit the reduced laser beam to form an opening in that portion of the epicardium which has been sucked into the concavity of the distal head end by a controlled vacuum. After the epicardium opening has been formed, the fiber bundle is advanced axially through it by the surgeon using a control on the hand-held device. At this point, the positioning means is expandable to allow passage therethrough of the fiber bundle which also passes through the opening in the epicardium. After passing through the epicardium opening, laser energy is emitted from the distal end of the optical fiber bundle as it is advanced by the surgeon into the myocardium tissue beyond the preliminary epicardium opening. Thus, the myocardium is ablated with the full beam of pulsed laser energy from said optical fiber distal end to form a channel as it moves into the left ventricular chamber. As the fiber element moves through the myocardium, an air suction conduit connected to the distal head end assembly provides a means for cleaning debris from the channel being formed and also for keeping the outer surface of the epicardium firmly against the stop member of the tip assembly. Sealing of the epicardium occurs after the fiber bundle is withdrawn, the vacuum is discontinued to release the epicardium with the concave distal end member, and the device is moved. Because the preliminary opening substantially closes at this point, a minimum of bleeding occurs after each TMR procedure. With the present device, the laser energy disbursed through the myocardium as a noncollimated, expanding beam creates a wider channel at the exit of the channel into the left ventricular cavity than within the myocardium so that revascularization can take place within the channel in the most effective manner.

Other objects, advantages and features of the present invention will be apparent to those skilled in the art from the following detailed description and the accompanying drawings.

DETAILED DESCRIPTION OF THE DRAWING

FIG. 1 is a schematic view in section of a human heart showing revascularization of the myocardium utilizing a device according to the present invention.

FIG. 2 is an enlarged view in perspective showing a device embodying principles of the invention for implementing the revascularization procedure of FIG. 1.

FIG. 3 is an enlarged exploded and fragmentary view in section of the device shown in FIG. 2 showing details of the handle portion and the advancing mechanism for linear movement of the movable fiber element.

FIG. 3A is a fragmentary view in section of the distal end member for the device shown in FIG. 3.

Fig. 3B is a sectional view of FIG. 3A with the optical fiber in a retracted position prior to advancement through the stop ring.

FIG. 3C is a sectional view of FIG. 3A with the optical fiber advanced past the stop ring.

FIG. 4 is an end view of the distal end member of the device of FIG. 3A.

FIGS. 4–9 are enlarged views in elevation and in section showing the end member of FIG. 3A assembled and in operation during a typical TMR procedure according to the invention.

DETAILED DESCRIPTION OF EMBODIMENT

With reference to the drawings, FIG. 1 diagrammatically depicts a human heart 10 with the epicardium 12 of the left ventricle 14 exposed where a Trans-Myocardial Revascularization (TMR) procedure according to the invention is to be performed. Preliminary to the procedure the surgeon makes an incision in the patient's chest to expose the outer wall of the heart's left ventricle. In a human heart the wall of the left ventricle, is comprised of an outer layer, the epicardium, the main muscle thickness or myocardium, and the inner layer or endocardium. The epicardium is comprised of a smooth, moist serous membrane which is somewhat tougher than the other tissue layers of the heart muscle.

In carrying out the method of the present invention, the surgeon utilizes a hand-held device 16 which is manipulated and operated to form a series of revascularization channels 18 in the myocardium of the patient's heart at selected spaced apart locations.

In accordance with the principles of the invention, each of the channels is formed by first penetrating the epicardium membrane with a restricted or reduced laser pulse to form a relatively small opening through which the distal end of an optical fiber bundle 26 can thereafter be forced to engage the myocardium. The fiber bundle is connected to a laser energy source 28 at its proximal end. Once through this epicardium opening, full beam laser energy is emitted in pulses from the distal end of the fiber bundle 26 as it is moved forwardly to form the channel 18 in the myocardium and completely through the endocardium. After the channel has been formed, the distal end of the fiber bundle is retracted to a position within the end member of the device 16 which can then be moved to another location to repeat the procedure. In a typical TMR procedure a number of channels, e.g. 30–50 may be formed depending on the patient's condition. When the end member of the device is removed, the relatively small opening in the epicardium substantially closes due to the tissue resiliency, thereby minimizing any blood flow from the channel just formed.

As shown in FIG. 2, the device 16 comprises a housing 20 adapted to be hand held by the surgeon during an operative procedure, a J-shaped neck member 22 attached to the housing and an interchangeable distal head member 24 having a disk like shape with concave surface 25 for contacting the outer surface of the epicardium membrane.

An optical fiber bundle 26 whose proximal end is connected to the laser source 28 extends through the housing and through the neck member to the distal end member 24. Within the housing 20 the fiber bundle 26 is connected to a movable shuttle 30 (FIG. 3) which extends outside the housing and is connected to a thumb actuated control member 32. Thus, movement of the control member 32 by the surgeon will move the distal end 34 of the fiber bundle beyond the concave surface 25 of the distal head member 24. The vacuum line 36 extending from the vacuum source 37, such as a conventional hospital vacuum type canister device, is connected to a barbed inlet 38 in the housing 20. This inlet communicates with an air passage 39 around the fiber bundle that extends the to distal head member 24. Thus, when in use, a suction is provided at the distal head member 24 of the device 16 which performs two vital functions. First of all, the suction force draws the epicardium tissue firmly against the concave contacting face 25 of the distal head member 24 so that a relatively small opening 31 can be made in the epicardium muscle fibers to allow the distal end of the fiber bundle 26 to penetrate and engage the myocardium. As the fiber bundle is advanced by the surgeon beyond the epicardium opening and into the myocardium, laser pulses are produced from its distal end 34 to form a channel 18 through the myocardium. As the fiber bundle continues to advance, the air suction provided helps to remove debris caused by the laser and also to draw blood into the channel to assure that the revascularization process will commence properly. When the fiber bundle is retracted after forming a channel, the distal end member 24 is moved away and the opening in the relatively small epicardium closes naturally with a minimum of bleeding.

Describing now the device 16 in greater detail, with reference to FIG. 3. The housing 20, which may be molded from a suitable plastic material, has an enlarged central cavity 40 to accommodate the shuttle 30. The latter has a cylindrical portion which surrounds and is firmly attached to the fiber bundle 26. Attached to the cylindrical portion is a web portion 42 which extends through an axial slot 44 in the housing. The web portion is connected to the control member 32 on the outside of the housing 20 which preferably has an arcuate configuration in cross section with a pair of external, transverse ridge portions 46 that facilitate easy thumb control by the surgeon.

Below the central cavity 40 is the barbed inlet 38 for the vacuum line 36 which communicates with the air passage 39 to the distal end member 24. An internal rubber disk 48 is provided within the housing to seal the air passage from the central cavity 40. The disk surrounds the fiber bundle and is held in place along its periphery by an annular groove 49.

At its forward end, the housing tapers to a threaded end portion 50 having a tapered end surface 52 for receiving a flared end 54 of the neck member 22. With the inner surface of this flared end in contact with the tapered end surface 52, a jam nut 56 around the neck member can be tightened on the threaded end portion 50 to secure the neck member to the housing 20.

The proximal end of the optical fiber bundle 26 is connected to the source or generator 28 of laser energy which is preferably a Holmium laser that operates at a wave length in the range of 1.8 to 2.2 microns and a pulse frequency in the range of 2-25 Hertz. This type of laser is preferable because it provides high absorption efficiency, hemostosis and a moderate absorption range in myocardium tissue, and is compatible with optical fiber delivery. A conventional foot switch (not shown) can be used by the surgeon to control the laser energy during a procedure.

At the laser generator, laser energy is supplied to the optical fiber bundle 26 which, at its distal end, has a diameter of around 1.5 mm. The optical fiber bundle is comprised of a plurality (e.g. 37) of glass fibers 32 each having a diameter of 100 microns. These glass fibers are held together by a suitable plastic material, such a 353 ND Epoxy, and near its distal tip, the bundle is preferably surrounded by an annular tantalum marker which serves to retain the bundle in a closely packed geometric boundary surrounding the bundled fibers is a plastic protective sheath such as polypropelene having a wall thickness of 0.004 inches. Other fiber bundle configurations could be used within the scope of the invention.

In the embodiment shown, the neck member 22 of the device 16 is a tubular member having a uniform outside diameter (e.g. 0.120 inches) and inside diameter (e.g. 0.094 inches) preferably bent into an angular "J" shape within which the optical fiber bundle 26 is slidable. This neck portion is preferably made from a stainless steel which may be heat treated to make it malleable and thus somewhat flexible. This enables the neck portion to be easily bent so that its distal end head member 24 can be positioned to accommodate the specific requirements of the surgical procedure being performed.

Removably attached to the distal end of the tubular neck is the enlarged disk-like head member 24 for the device 16. In the embodiment shown in FIGS. 3A to 3C, the head member 24 has an annular flange portion 27 with its previously described generally concave surface 25 that surrounds a central opening 28 therein. Preferably, this head member 24 is made of a molded plastic material such as nylon, which allows the flange portion 27 to be slightly flexible. One or more concentric circular ridges 29 with sharp outer edges are provided in the end surface 25 so that the head member 24 will retain its position when pressed firmly against the epicardium of a beating heart.

In accordance with this invention, the initial opening 31 in the epicardium is made by a laser beam of somewhat reduced diameter before the fiber bundle 26 is caused to proceed forwardly through the myocardium. Here, the circular distal head member 24 with its concave inner surface is moved toward against the outer surface of the epicardium, as shown in FIG. 4. At the center of the concave surface 25 the opening 28 communicates with an axial bore 60 which is smooth along its inner end and has internal threads at an extended neck portion 62. These internal threads enable the distal tip member 24 to be easily attached to and removed from the threaded end of the neck portion 22 of the device 16. Just inside the smooth bore 60 is a circular groove 64 for retaining a split, flexible stop ring 66. In its relaxed state this stop ring has a diameter slightly smaller than the bore 60, and it provides a temporary stop and positioning means for the distal end 34 of the fiber bundle 26. This stop ring is preferably made of resilient metal which is preferably gold or copper plate to provide a heat sink and thus a means for shielding or blocking a peripheral portion of the laser beam emitted from the distal end of the fiber bundle. In essence, it enables the surgeon to place the laser emitting distal end 34 of the fiber bundle against the stop ring at precisely the desired stand-off distance from the epicardium to create the desired initial opening therein, as shown in FIG. 5. Since the stop ring shields the outer periphery of fiber bundle, only a laser beam of a smaller diameter can pass through the stop ring to strike the epicardium membrane.

The method of operation for the device 16 using the concave distal head member 24 is illustrated in FIGS. 4 to 9. As shown in FIG. 4, the surgeon first manipulates the device 16 so that concave surface 25 of the distal head member 24 can be moved against the outer surface of the epicardium. At this point, as shown in FIG. 5, the vacuum pressure supplied through tube 36 to the device 16 is furnished through the central opening 28 of the distal head member and causes the epicardium to bulge into the concavity of its flange portion 27. This stretches the epicardium membrane to some extent. At almost the same instant, the surgeon moves the fiber bundle 26 forward until its distal end 34 is stopped momentarily by the stop ring member 66 at the desired distance from the epicardium. Now, a laser pulse is initiated from the distal end 34 of the fiber bundle 26 to make the preliminary opening 31 in the stretched epicardium membrane. (FIG. 6) Since the expandable stop ring has a small inside diameter it reduces the size of the laser beam that strikes the epicardium. After this opening has been formed, the surgeon again uses the device control 32 to advance the fiber bundle 26, as shown in FIG. 7. As this is done, the distal end 34 of the fiber bundle moves forwardly through the stop ring 66, causing it to expand radially into its groove 64, and the distal end of the fiber bundle then moves into the myocardium. Simultaneously, laser pulses with a full beam diameter are emitted from the distal end of the fiber bundle as it moves forward to form a channel 18 all of the way through the myocardium and the endocardium, as shown in FIG. 7. After the channel has been completed, the fiber bundle 26 is retracted back inside the distal end member 24 and inwardly from the ring member 66, as shown in FIG. 8, to be ready for forming the next channel. As the channel is being formed and during retraction of the fiber bundle, a vacuum through the distal head 24 is maintained which helps to remove debris from the channel 18 and also to draw blood into it to start the revascularization process. After full retractions of the fiber bundle, using the device control 32, the removal of the concave flange member 26 from the epicardium, as shown in FIG. 9, allows the membrane to resume its normal shape which tends to close the initial opening 31 formed therein, thereby preventing excessive bleeding.

From the forgoing it is apparent that the present invention provides an improved device for performing TMR procedures that combines simplicity with efficiency to enable the formation of effective channels for revascularization which will normally close at the epicardium membrane to minimize post-operative bleeding To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A transmyocardial revascularization (TMR) hand-held device for performing TMR on a patient's heart, the device comprising:

a handle portion;

a tubular neck portion connected to the handle portion;

a head portion on a distal end of the tubular neck portion, the head portion forming a distal end contact surface;

an optical fiber having a proximal end configured for connecting to a laser energy source, the optical fiber extends through the handle portion, the neck portion and the head portion;

an adjustment means disposed on the handle portion for moving the optical fiber within the handle and neck portions and head portion; and irradiation control means for providing reduced laser pulse energy from the optical fiber's distal end at a first position proximate to the epicardium thereby enabling formation of a pilot hole in the epicardium, wherein the optical fiber can thereafter be moved axially from the first position by the adjustment means and allow nonreduced laser energy to emanate from the optical fiber's distal end whereby enabling formation of a myocardial revascularization channel.

2. The device of claim 1 wherein the irradiation control means is a means for partially shielding the optical fiber's distal end whereby laser beam energy therefrom is reduced.

3. The device of claim 1 wherein the head portion has a concave end face.

4. The device of claim 3 wherein the head portion includes at least one opening on the distal end contact surface, the at least one opening communicates through a tubular member extending through the handle portion, the tubular member is configured for connecting to a vacuum source, whereby activation of the vacuum source: a) draws the epicardium against the distal end contact surface, b) assists in ablated tissue removal and c) draws blood into the revascularizing channel.

5. The device of claim 1 wherein the adjustment means includes within the handle portion an axial lumen, a movable shuttle within the axial lumen that is connected to the optical fiber, the optical fiber extends axially within the lumen, and a control knob attaches to the shuttle and extends outwardly from the handle portion, whereby the optical fiber can axially move within the handle portion by moving the control knob.

6. The device of claim 1 including at a central opening of the head member a sensing means for predetermined positioning of the optical fiber's distal end relative to the epicardium.

7. The device of claim 6 wherein the sensing means responds to increased axial force from the optical fiber thereby allowing the optical fiber to pass through the central opening and egress into myocardial tissue.

8. The device of claim 6 wherein the sensing means includes an expandable split ring that seats within a groove in the central opening.

9. The device of claim 8 wherein the split ring has an inner diameter that is less than the diameter of the optical fiber whereby when the optical fiber's distal end urges against the split ring and emits laser energy, the slit ring partially shields laser irradiation from the optical fiber thereby forming a pilot hole in the epicardium.

10. The device of claim 9 wherein the split ring has a metal alloy coating that absorbs laser energy.

11. The device of claim 1 wherein the head portion forming the distal end contact surface includes at least one circular ridge member for positional stability.

12. The device of claim 1 wherein the head portion includes a means for attaching to the tubular neck portion.

13. The device of claim 1 further including rotational adjusting means for radially orienting the neck portion relative to the handle portion.

14. The device of claim 13 wherein the rotational adjusting means is a jam nut disposed on the neck portion which threadedly attaches to the handle portion.

15. The device of claim 1 wherein the tubular neck portion has an offset curved shape at the neck portion's distal end and is made of a malleable material thereby allowing changes of the head portion's orientation relative to the handle portion.

16. A method for myocardial revascularization of a patient's heart comprising the steps of:

a) providing access to the patient's heart and positioning an optical fiber whose proximal end connects to a laser source and whose distal end is for laser pulse emissions, the optical fiber's distal end initially is juxtaposed to an irradiation control means for providing reduced laser pulse emissions from the optical fiber at an initial position;

b) placing the optical fiber's distal end near the heart's surface at the initial position;

c) pulsing the laser source at the initial position forming a pilot hole in the epicardium;

d) advancing the optical fiber past the irradiation control means through the pilot hole; and e) pulsing the laser source while advancing the optical fiber's distal end into the heart's myocardium thereby allowing non-reduced laser energy to emanate from the optical fiber's distal end and forming a revascularizing channel.

17. The method of claim 16 wherein in step a) of providing a revascularizing device with the optical fiber, the device further includes a head portion on a distal end of a tubular neck portion, the head portion has an opening on the distal end's contact surface communicating through a tube to a vacuum source; and prior to the step c), applying suction to the distal end's contact surface thereby causing the epicardium to be drawn firmly against the distal end's contact surface.

18. The method of claim 16 further including the step of applying suction to the distal end's contact surface as the optical fiber is moving during channel formation in step e).

19. The method of claim 16 further including the steps of withdrawing the optical fiber and continuing to apply suction to the distal end's contact surface thereby drawing blood into the revascularizing channel, thus increasing myocardial revascularization and removing ablated tissue.

* * * * *